United States Patent [19]

Karol et al.

[11] Patent Number: 5,177,212

[45] Date of Patent: Jan. 5, 1993

[54] PHENOLIC DERIVATIVES OF 2,5-DIMERCAPTO-1,3,4-THIADIAZOLES

[75] Inventors: Thomas J. Karol, Norwalk; Steven G. Donnelly, Fairfield, both of Conn.

[73] Assignee: R.T. Vanderbilt Company, Inc., Norwalk, Conn.

[21] Appl. No.: 736,146

[22] Filed: Jul. 26, 1991

[51] Int. Cl.$^5$ ................... C07D 285/12; C10M 1/38
[52] U.S. Cl. ................................. 548/142; 252/47; 252/47.5
[58] Field of Search .................. 548/142; 252/47, 47.5

[56] References Cited

U.S. PATENT DOCUMENTS

| | | | |
|---|---|---|---|
| 2,703,784 | 3/1955 | Fields | 252/32.7 |
| 2,703,785 | 3/1955 | Roberts et al. | 252/33.4 |
| 2,749,311 | 6/1956 | Sabol et al. | 252/32.7 |
| 2,799,651 | 7/1957 | Richardson et al. | 252/32.7 |
| 2,850,453 | 9/1958 | Fields | 252/32.7 |
| 3,676,449 | 7/1972 | Song | 260/302 SD |
| 4,410,703 | 10/1983 | Okorodudu | 548/142 |
| 4,734,457 | 3/1988 | Doe | 525/149 |
| 4,803,211 | 2/1989 | Mase | 514/361 |
| 4,904,403 | 2/1990 | Karol | 252/47.5 |

*Primary Examiner*—Robert Gerstl
*Attorney, Agent, or Firm*—Rasma B. Balodis

[57] ABSTRACT

Disclosed are novel compounds prepared by reacting 2,5-dimercapto-1,3,4-thiadiazole, aliphatic or aromatic aldehyde and alkylated phenol in the molar ratio of 1:1:1 to 2:2:1. The 2,5-dimercapto-1,3,4-thiadiazole may be substituted in the 2-position by terpene, polymeric and succinate residues. The compounds are effective antiwear agents and antioxidants when incorporated into lubricating compositions.

4 Claims, 1 Drawing Sheet

PHENOLIC DERIVATIVES OF 2,5-DIMERCAPTO-1,3,4-THIADIAZOLES

BACKGROUND OF THE INVENTION

The present invention concerns novel phenolic derivatives of thiadiazole compounds and their use as multifunctional additives for lubricating compositions. More particularly, the novel thiadiazoles are derived from 2,5-dimercapto-1,3,4-thiadiazole, an aldehyde and a phenolic compound.

Additives known as antiwear agents are employed to increase the load-carrying capacity of lubricants. The antiwear additives promote the formation of a surface film and thereby prevent wear of the contacting metal surfaces.

During the course of use, lubricants are susceptible to deterioration due to oxidation. The oxidative process leads to the loss of lubricating properties and inadequate protection of the device to be lubricated. Antioxidants are added to inhibit the oxidative process. Therefore, it is desirable that antiwear agents possess antioxidant properties.

U.S. Pat. No. 2,850,453 discloses symmetrical phenolic derivatives of 1,3,4-thiadiazole which possess corrosion and oxidation inhibiting properties when incorporated into lubricating oils. However, due to stricter environmental controls, there is a need for new and more effective ashless-type additives, preferably possessing multifunctional properties.

SUMMARY OF THE INVENTION

In accordance with the invention, there are provided novel phenolic 1,3,4-thiadiazole compounds having the structural formulae:

(a)

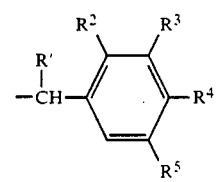

(I)

wherein R represents hydrogen, terpene residue, polymeric residue having 20 to 200 carbon atoms and succinate residue of the formula:

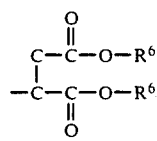

$R'$ represents hydrogen, $C_{1-17}$-alkyl, phenyl and phenyl substituted by alkyl groups; $R^2$ and $R^4$ represent hydrogen, hydroxy and alkyl groups provided that either $R^2$ or $R^4$ is hydroxy; $R^3$ and $R^5$ are alkyl groups; $R^6$ represents hydrogen, alkyl and cycloalkyl groups;

(b)

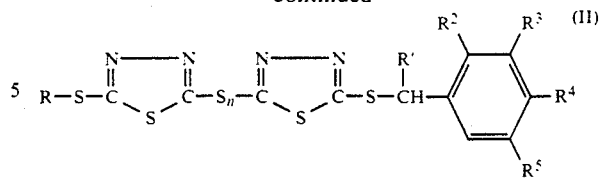

(II)

wherein n = 1-2,
R represents hydrogen, terpene residue, polymeric residue and succinate residue as defined above and phenyl group of the formula

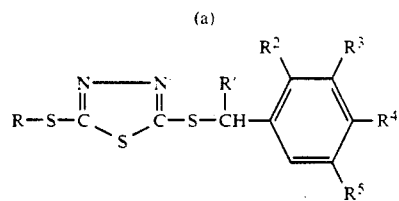

and $R'$, $R^2$, $R^3$, $R^4$, and $R^5$ have the above meaning; and (c)

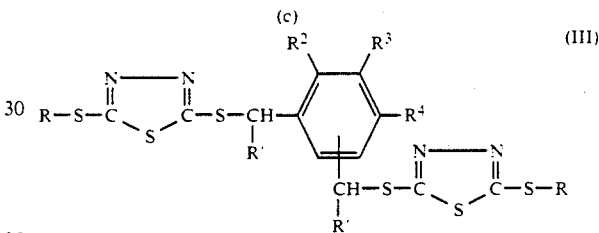

(III)

wherein R, $R'$, $R^2$, $R^3$, and $R^4$ have the above meaning.

Another aspect of the invention concerns improved oil-based lubricating compositions comprising a major amount of base oil and an effective amount to impart antiwear and antioxidant properties to said composition, of a 1,3,4-thiadiazole characterized by formulae I, II and III.

A further aspect of the invention concerns a method for protection of metal surfaces from wear by applying improved lubricating oil compositions, the improvement of which consists of adding to the composition an effective amount of a 1,3,4-thiadiazole compound characterized by the structural formula I, II and III.

FIG. 1 shows the infrared spectrum of the compound of the invention, bis(pinanylthio-1,3,4-thiadiazole-5-thiomethylene) derivative of phenol. The spectrum shows band transmission of phenolic OH-absorption at wavenumber 3106 to 3300 cm$^{-1}$.

DESCRIPTION OF SPECIFIC EMBODIMENTS

Figure 1:
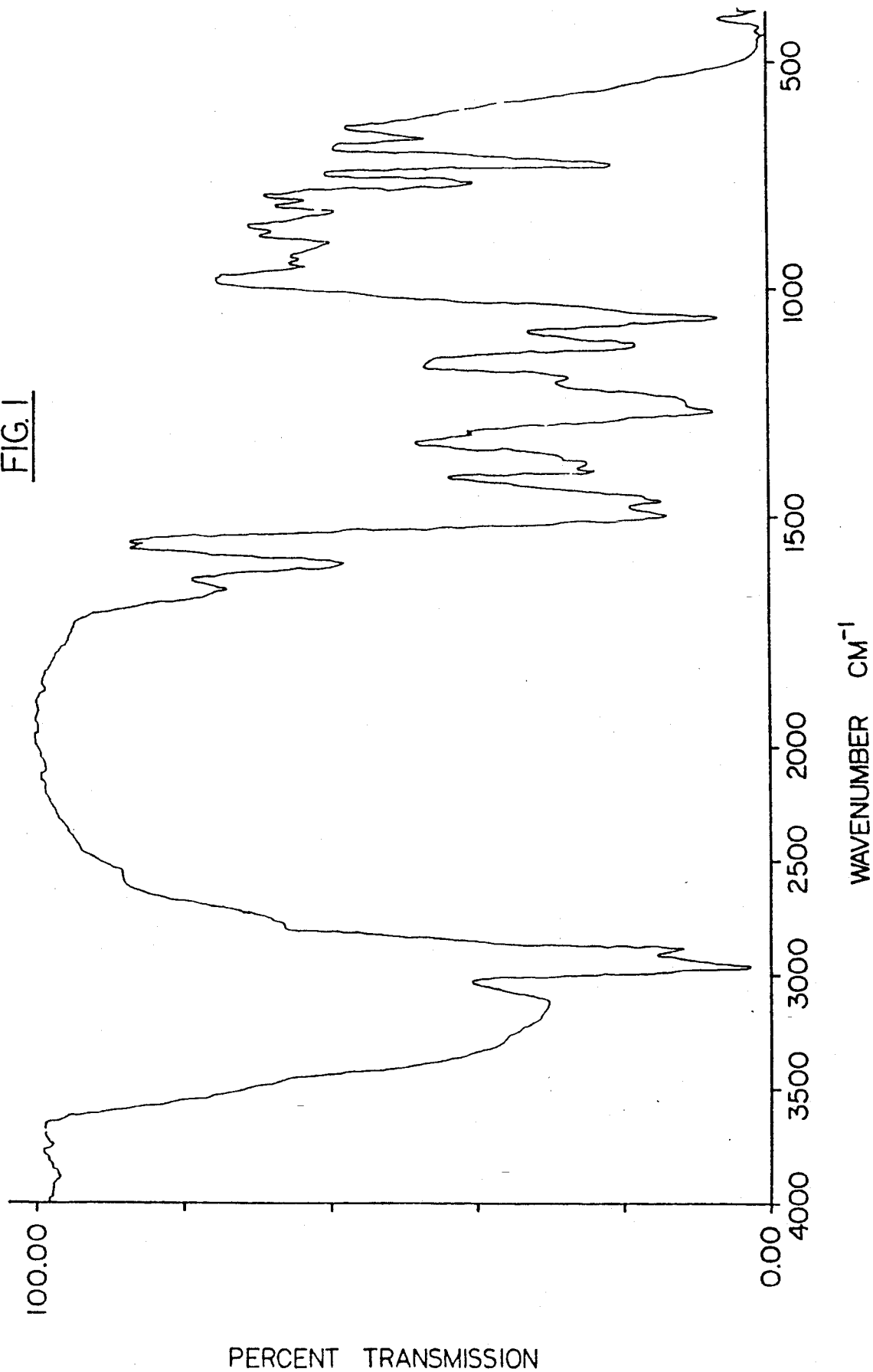

The novel compounds of the invention may be prepared by reacting 2,5-dimercapto-1,3,4,-thiadiazole, aldehyde and a phenol in the molar ratio of 1:1:1 to 2:2:1. The reaction is essentially an alkylation process wherein the 2,5-dimercapto-1,3,4-thiadiazole and aldehyde form an intermediate and the latter attaches to the phenol ring. The hydroxy group of the phenol does not enter into the reaction as evidenced by infrared spectra. A band indicative of free hydroxy group appears in the 3105 to 3700 cm$^{-1}$ range. The actual band width depends somewhat on the structure of a specific compound.

A possible by-product of the main reaction may be an ether formed by the intermediate and the hydroxy group of the phenol. To decrease the amount of the ether by-product, the phenol reactant may be capped with lower molecular weight carboxylic acid or anhydride and then reacted with the intermediate to form the alkylated phenolic product in higher yields. The capping group is subsequently removed by hydrolysis. The method is particularly preferred for preparation of dialkylated products. The reaction may be conducted in the presence or absence of a suitable inert solvent, such as hexane, toluene, dimethyl ether and others. Optionally, the reaction may employ acid catalysts as for example Lewis acids. Exemplary carboxylic acids and anhydrides include, among others, acetic, formic, propionic and butyric acids or anhydrides.

The aldehyde reactant may be a normal or branched chain aliphatic aldehyde containing 1 to 18 carbon atoms or an aromatic aldehyde. Examples of suitable aldehydes include, among others, formaldehyde, acetaldehyde, benzaldehyde, 2-ethylehxyl aldehyde, butyraldehyde, caprylic aldehyde, phenylacetaldehyde, and salicylaldehyde.

The phenol compound may be substituted by alkyl groups. Examples of suitable compounds include hindered phenols such as 2,5-tert-butylphenol, nonylphenol, octylated phenol and 3-pentadecylphenol.

The novel phenolic derivatives of 1,3,4-thiadiazole may be substituted in the 5-position by terpene residues, polymeric residues and succinate residues. Particularly preferred terpene residues are pinene residue of the formula:

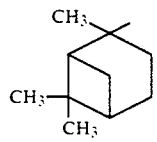

and limonene residue of the formula:

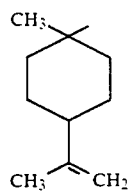

The polymeric residue is essentially a hydrocarbyl radical having 20 to 200 carbon atoms. Typically, the molecular weight of the polymeric residue ranges from 280 to 2600 and higher. Preferred are polymers having olefinic unsaturation. The polymers may have straight or branched chain aliphatic units having 2 to 10 carbon atoms. Especially useful are polymers and copolymers of alpha-olefins as for example isopropene, isobutene, 2-methyl-1-heptene, ethylene, propylene, and 2-methyl-5-propylhexene. The polymeric residue may be derived from a hydrocarbon polymer with an epoxide or chlorine functionality. Activated polyolefins are available commercially. Activated polyisobutenes with epoxide functionality are marketed under the trade name AC-TIPOL TM by Amoco Chemical Company. Alternately, commercial polyolefins may be epoxidized by known methods.

The succinate residue in the above formulae may be derived from maleic anhydride or acid and further esterified with normal and branched chain alkyl groups containing 1 to 22 carbon atoms and cyclic aliphatic groups such as cyclohexyl, cyclopentyl and cycloheptyl.

The thiadiazole derivatives of the invention are useful as additives for lubricants. The compounds possess multifunctional properties. In addition to being effective antiwear agents, they also perform oxidation inhibiting functions.

The lubricating compositions contemplated herein include lubricating oils and lubricating greases containing a major amount of base oil. The base oil may be selected from naphthenic, aromatic, paraffinic, mineral and synthetic oils. The synthetic oils may be selected from, among others, alkylene polymers, polysiloxanes, carboxylic acid esters and polyglycol ethers.

The amount of the thiadiazole additive required to be effective for imparting antiwear and antioxidant characteristics to lubricating compositions may range from about 0.01 to 15.0 percent of the lubricating composition. The preferred range is about 0.1 to 5.0 percent of the additive based on the weight of the lubricating composition.

The lubricating compositions may contain the necessary ingredients to formulate the composition, as for example emulsifiers, dispersants and viscosity improvers. Greases may be prepared by adding thickeners, as for example, salts and complexes of fatty acids, polyurea compounds, clays and quaternary ammonium bentonite complexes. Depending on the intended use of the lubricant, other functional additives may be added to enhance a particular property of the lubricant. The lubricating compositions may further contain extreme pressure agents, metal passivators, rust inhibitors, dispersants and other known antioxidants and antiwear agents.

The following examples are given for the purpose of further illustrating the invention. All percentages and parts are based on weight unless otherwise indicated.

EXAMPLE 1

A reactor was charged with alpha-pinene, 75 g, 2,5-dimercapto-1,3,4-thiadiazole, 75 g, 70% solution of methanesulfonic acid, 1.5 g, and slowly heated to 130° C. After heating for half an hour, the reaction was stripped of excess pinene under vacuum.

The phenol reactant was capped by reacting phenol, 47 g, and acetic anhydride, 55 g, for 3 hours at 130° C. The product was extracted with water/hexane, then extracted with sodium carbonate solution, and dried over magnesium sulfate.

The capped phenol was added to the thiadiazole reactant, followed by 70% methanesulfonic acid, 1.5 ml, and 90% paraformaldehyde, 25 g. The reactor was fitted with Dean Stark attachment, filled with hexane, and heated to 120° C. to remove water. The product was stripped. The reaction was charged with 50% sodium hydroxide solution, 45 g, and refluxed for 2 hours. The product was extracted with a solution of ethyl ether and dilute sulfuric acid, and dried over magnesium sulfate. The yield was 81 percent.

EXAMPLE 2

A reactor fitted with Dean-Stark attachment was charged with 2-pinanyl-1,3,4-thiadiazole prepared as in Example 1, 90% paraformaldehyde, 17 g, 2,6-di-t-butylphenol, 104.7 g, and 70% solution of methanesulfonic acid, 1.5 ml and heated to 130° C. The reaction was cooled to 80° and 50% sodium carbonate solution was slowly added. The water was stripped off and the product was filtered.

The IR spectrum showed a free hydroxy band at 3662 cm$^{-1}$.

EXAMPLE 3

A reactor was charged with 2,5-dimercapto-1,3,4-thiadiazole, 15 g, paraformaldehyde, 3.2 g, 2,6-di-t-butylphenol, 21 g, and hexane azeotroping solvent, 40 ml. The reaction was heated to 122° C. to remove water. Solvent was removed by applying vacuum.

EXAMPLE 4

A reactor fitted with Dean-Stark attachment was charged with 5,5'-dithiobis-1,3,4-thiadiazole-2(3H)-thione, 20 g, paraformaldehyde, 4.5 g, 2,6-di-t-butylphenol, 28 g, and hexane azeotroping solvent, 30 ml. The reaction was heated to remove water. After cooling to room temperature, the product was dried over magnesium sulfate, filtered through a filter aid and stripped of solvent under vacuum.

EXAMPLE 5

A reactor was charged with epoxidized polyisobutylene, mol. wt. 1000, 876.4 g, hexane, 208.6 g, and isopropyl alcohol, 208.6 g. 2,5-Dimercapto-1,3,4-thiadiazole, 102.2 g, was added with stirring and the reaction was maintained overnight. Paraformaldehyde, 26 g, was charged to the reactor equipped with Dean-Stark attachment and heated to reflux. The product was filtered and stripped of solvent.

The above product, 92.5 g, 2,6-di-t-butylphenol, 13.9 g, toluene, 150 ml, and 70% methanesulfonic acid, 0.25 ml, were added and heated to reflux. Water was azeotroped off. Sodium carbonate, 5 g, was added. The product was filtered and stripped of solvent.

EXAMPLE 6

A reactor was charged with 2-(1,2-di(2-ethylhexoxycarbonyl)ethylthio)-1,3,4-thiadiazole-5-thiol, 1400.4 g, and paraformaldehyde, 118 g and heated with stirring at 130°–135° C. for 2 hours. The intermediate was recovered by filtering.

The intermediate, 151.09 g, 2,6-di-t-butylphenol, 62 g, toluene, 75 ml, and 70% methanesulfonic acid, 1.53 g, were charged to a reactor equipped with Dean-Stark attachment and refluxed at 120°–130° C. After removal of water, the product was stripped of solvent and filtered.

EXAMPLE 7

Modified Falex Wear Test

A laboratory test was conducted by using the original Falex machine to simulate the valve train wear of an automobile engine. The V-blocks and pin were washed in mineral spirits with an ultrasonic cleaner, rinsed with acetone, air-dried and weighed. The test sample (60 g) was placed into the oil cup. The motor was switched on and the loading arm was placed on the ratchet wheel. Upon reaching the reference load of 227 kg, the ratchet wheel was disengaged and the load was maintained constant for 3.5 hours. Thereafter, the motor was switched off. The V-blocks and pin were washed, dried and weighed. The weight loss, a measure of wear, was recorded and compiled in Table I.

The test samples were prepared by adding the compounds of the invention to the base motor oil SAE 30, SF (containing 0.11 percent phosphorus and no supplemental antioxidant) in the amount given in Table I. The results indicate that the present compounds afford good antiwear properties.

TABLE I

| | Modified Falex Wear Test | | |
|---|---|---|---|
| Sample | Active Ingredient | Percent | Total Weight Loss, mg. |
| 1 | None | — | 57.2 |
| 2 | 5-(3,5-Di-t-butyl-4-hydroxyphenyl-methylthio)-1,3,4-thiadiazole-2-thiol | 0.35 | 35.3 |

EXAMPLE 8

Thin Film Oxygen Uptake Test

The test was conducted essentially according to the method described by Chia-Soon Ku et al, *J. Am. Soc. Lubricating Eng.*, 40, 2 75–83, 1984. The oxidation induction time of the lubricant was measured under conditions which simulate the high temperature oxidation processes in automotive engines by a modified rotary bomb oxidation test method ASTM D-2272. The test was conducted with 1.5 gram samples of SAE 30, SF motor oil. The oil was fully formulated with the exception of the antioxidant additives. A compound of the invention, 2-(1,2-di-(2-ethylhexoxycarbonyl)ethylthio-5-(3,5-di-t-butyl-4-hydroxyphenylmethylthio)-1,3,4-thiadiazole, was added to the oil in the amount indicated in Table II. The test was conducted at 160° C., and initial oxygen pressure of 620.6 kPa (90 psi). A "pass" oil has a high induction time, while a "fail" oil has a low time. The additive of the invention has good antioxidant properties as indicated by the data compiled in Table II.

TABLE II

| | Thin Film Oxygen Uptake Test | | |
|---|---|---|---|
| Sample | Active Ingredient | Percent | Average Induction Time, Min. |
| 3 | None | — | 108 |
| 4 | 2-(1,2-di(2-ethylhexoxycarbonyl)ethylthio)-5-(3,5-di-t-butyl-4-hydroxyphenylmethylthio)-1,3,4-thiadiazole | 0.35 | 139 |

EXAMPLE 9

Extreme Pressure Tests

The load carrying properties of a lithium 12-OH stearate grease containing the compounds of the invention were tested essentially according to the method described in ASTM D2596-87. The test was conducted at a rotating speed of 1800 rpm at 27°±8° C. The test samples were subjected to a series of tests of 10 second duration at increasing loads until welding of the balls occurred. The weld point measured in kgf indicates that the extreme pressure level of the grease has been exceeded.

The test was repeated in polyol ester base at a rotating speed of 1800 rpm at 54.4° C. The results compiled in Table III demonstrate that the compounds of the invention possess extreme pressure properties.

TABLE III

| | | Extreme Pressure Test | | |
|---|---|---|---|---|
| Sample | Base | Active Ingredient | Percent | Weld Point, kgf |
| 5 | Grease | — | — | 160 |
| 6 | Grease | Product of Example 4 | 2.0 | 250 |
| 7 | Polyol ester | — | — | 126 |
| 8 | Polyol ester | Product of Example 4 | 2.0 | 250 |

The above embodiments have shown various aspects of the present invention. Other variations will be evident to those skilled in the art and such modifications are intended to be within the scope of the invention as defined by the appended claims.

What is claimed is:

1. A phenolic 1,3,4-thiadiazole compound selected from the group of compounds having the structural formulae:

(a)

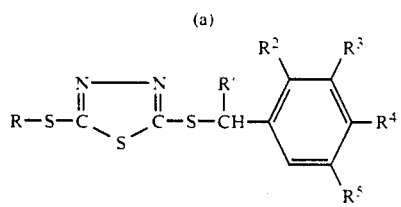

wherein R represents hydrogen, terpene residue selected from the group consisting of pinene and limonene, polymeric residue having 20 to 200 carbon atoms and derived from polyolefins or activated polyolefins having an epoxide or chlorine functionality, and succinate residue of the formula:

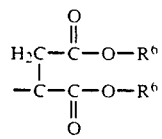

R' represents hydrogen, $C_{1-17}$-alkyl, phenyl and phenyl substituted by alkyl groups; $R^2$ and $R^4$ represent hydrogen, hydroxy and alkyl groups provided that either $R^2$ or $R^4$ is hydroxy; $R^3$ and $R^5$ are alkyl groups; $R^6$ represents hydrogen, $C_{1-22}$-alkyl and cycloalkyl groups;

(b)

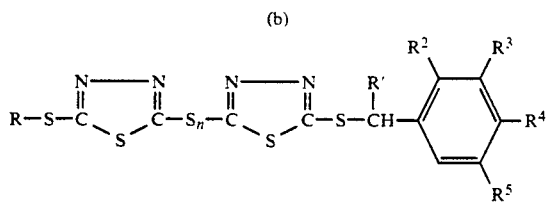

wherein n=1-2,
R represents hydrogen, terpene residue selected from the group consisting of pinene and limonene, polymeric residue having 20 to 200 carbon atoms and derived from polyolefins or activated polyolefins having an epoxide or chlorine functionality, and succinate residue as defined above and phenyl group of the formula:

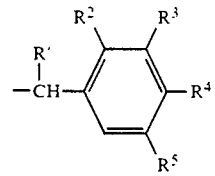

and R', $R^2$, $R^3$, $R^4$ and $R^5$ have the above meaning and (c)

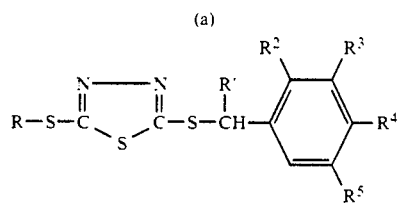

wherein R, R', $R^2$, $R^3$ and $R^4$ have the above meaning.

2. A lubricating composition comprising a major portion of an oil of lubricating viscosity and a minor antiwear and oxidation inhibiting amount of a compound selected from the group consisting of compounds having the structural formulae:

(a)

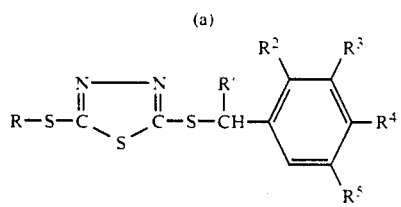

wherein R represents hydrogen, terpene residue selected from the group consisting of pinene and limonene, polymeric residue having 20 to 200 carbon atoms and derived from polyolefins or activated polyolefins having an epoxide or chlorine functionality, and succinate residue of the formula

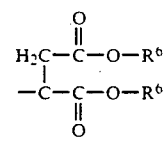

R' represents hydrogen, $C_{1-17}$-alkyl, phenyl and phenyl substituted by alkyl groups; $R^2$ and $R^4$ represent hydrogen, hydroxy and alkyl groups provided that either $R^2$ or $R^4$ is hydroxy; $R^3$ and $R^5$ are alkyl groups; $R^6$ represents hydrogen, $C_{1-22}$-alkyl and cycloakyl groups;

(b)

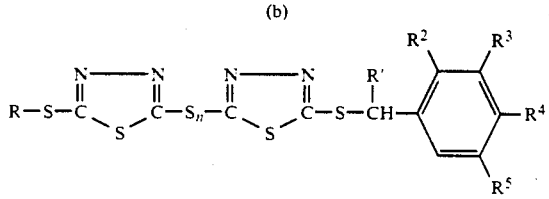

wherein n=1-2, R represents hydrogen, terpene residue selected from the group consisting of pinene and limonene, polymeric residue having 20 to 200 carbon atoms and derived from polyolefins or activated polyolefins having an epoxide or chlorine functionality, and succinate residue as defined above and phenyl group of the formula

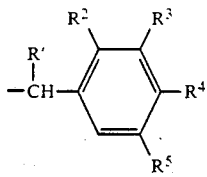

and R', R², R³, R⁴ and R⁵ have the above meaning, and (c)

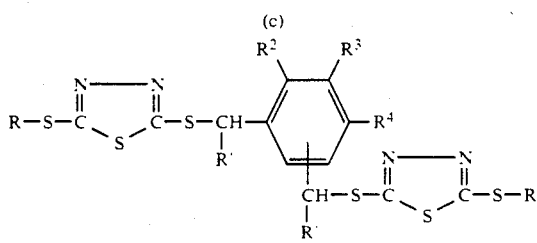

wherein R, R', R², R³ and R⁴ have the above meaning.

3. A lubricating composition according to claim 2 which contains a thickener.

4. A Method for protecting metal surfaces from wear which comprises contacting the surfaces with a lubricating composition comprising a major amount of base oil of lubricating viscosity, the improvement of which consists of adding to the oil a minor antiwear and oxidation inhibiting amount of an additive selected from the group of compounds having the structural formulae (a)

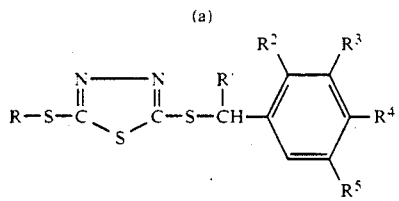

wherein R represents hydrogen, terpene residue selected from the group consisting of pinene and limonene, polymeric residue having 20 to 200 carbon atoms and derived from polyolefins or activated polyolefins having an epoxide or chlorine functionality, and succinate residue of the formula

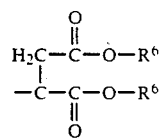

R' represents hydrogen, $C_{1-17}$-alkyl, phenyl and phenyl substituted by alkyl groups; R² and R⁴ represent hydrogen, hydroxy and alkyl groups provided that either R² or R⁴ is hydroxy; R³ and R⁵ are alkyl groups; R⁶ represents hydrogen, $C_{1-22}$-alkyl and cycloalkyl groups;

(b)

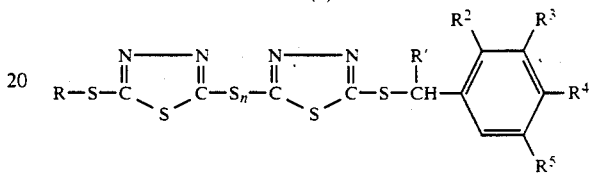

wherein n=1-2, R represents hydrogen, terpene residue selected from the group consisting of pinene and limonene, polymeric residue having 20 to 200 carbon atoms and derived from polyolefins or activated polyolefins having an epoxide or chlorine functionality, and succinate residue as defined above and phenyl group of the formula

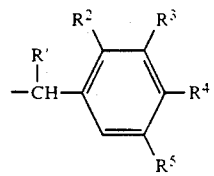

and R', R², R³, R⁴ and R⁵ have the above meaning, and (c)

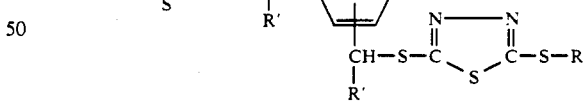

wherein R, R', R², R³ and R⁴ have the above meaning.

* * * * *

UNITED STATES PATENT AND TRADEMARK OFFICE
CERTIFICATE OF CORRECTION

PATENT NO. : 5,177,212

DATED : January 5, 1993

INVENTOR(S) : Thomas J. Karol, et. al.

It is certified that error appears in the above-indentified patent and that said Letters Patent is hereby corrected as shown below:

At col. 1, lines 55 to 60, the formula

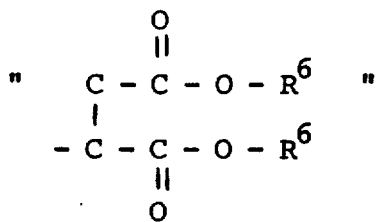

should be

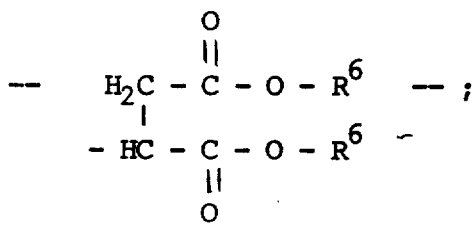

Column 3, line 20, "2-ethylehxyl" should be -- 2-ethylhexyl --.

UNITED STATES PATENT AND TRADEMARK OFFICE
CERTIFICATE OF CORRECTION

PATENT NO. : 5,177,212
DATED : January 5, 1993
INVENTOR(S) : Thomas J. Karol, et. al.

It is certified that error appears in the above-indentified patent and that said Letters Patent is hereby corrected as shown below:

At claim 1, col. 7, lines 40 to 45, claim 2, col. 8, lines 47 to 52, and claim 4, col. 10, lines 4 to 9 the formula        should be

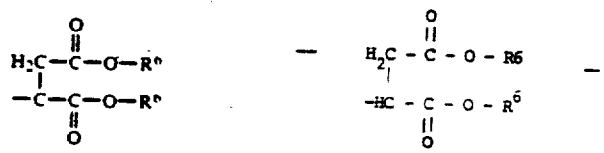

Signed and Sealed this

Twenty-seventh Day of December, 1994

Attest:

BRUCE LEHMAN

Attesting Officer      Commissioner of Patents and Trademarks